United States Patent [19]
Taylor et al.

[11] Patent Number: 5,177,262
[45] Date of Patent: Jan. 5, 1993

[54] PROCESS AND COMPOSITION FOR USE IN PHOTOGRAPHIC MATERIALS CONTAINING HYDROQUINONES

[75] Inventors: Lloyd D. Taylor, Lexington; John C. Warner, Norwood, both of Mass.

[73] Assignee: Polaroid Corporation, Cambridge, Mass.

[21] Appl. No.: 732,836

[22] Filed: Jul. 19, 1991

[51] Int. Cl.$^5$ ............................................ C07C 233/65
[52] U.S. Cl. ..................................... 564/156; 430/214
[58] Field of Search ........................................ 564/156

[56] References Cited

U.S. PATENT DOCUMENTS

| | | | |
|---|---|---|---|
| 2,627,460 | 2/1953 | Land | 95/8 |
| 2,983,606 | 5/1961 | Rogers | 96/29 |
| 3,362,819 | 1/1968 | Land | 96/3 |
| 3,719,489 | 3/1973 | Cieciuch et al. | 96/29 D |
| 3,914,187 | 10/1975 | Fein et al. | 260/2.5 B |
| 3,954,682 | 5/1976 | Fein et al. | 260/2.5 B |
| 3,988,318 | 10/1976 | Copes et al. | 260/239.3 R |
| 3,988,350 | 10/1976 | Copes et al. | 260/326.5 FL |
| 3,998,351 | 10/1976 | Copes et al. | 260/326.25 |
| 4,058,462 | 11/1977 | Fein et al. | 210/289 |
| 4,293,641 | 10/1981 | Takahashi et al. | 430/502 |
| 4,740,448 | 4/1988 | Kliem | 430/214 |
| 4,942,107 | 7/1990 | Saeki | 430/138 |
| 4,946,967 | 8/1990 | Login et al. | 548/531 |

OTHER PUBLICATIONS

Lee, W. E. and Brown, E. R., in Chapter 11 of James, T. H. (ed.), The theory of the photographic process, Macmillan, New York (1977).

Walworth, V. K. and Mervis, S. H., Instant photography and related reprographic processes, in Sturge, J., Walworth, V. K., and Shepp, A. (eds.), Imaging materials and processes—Neblette's eighth edition, Van Nostrand Reinhold, New York, NY (1989).

Beilstein, Handbuch der Organische Chemie, E IV 9, p. 3321, Syst-Nr. 978/H 845, E III, p. 4253.

Primary Examiner—Richard L. Raymond
Attorney, Agent, or Firm—David J. Cole

[57] ABSTRACT

Hydroquinones form stable hydrogen-bonded complexes with N,N,N',N'-tetrasubstituted diamides of aromatic dicarboxylic acids in which two carboxyl groups are arranged para to one another on the same phenyl ring. These complexes are useful in rendering the hydroquinones more water-dispersible to assist their incorporation into photographic products. Also, the diamides may be incorporated into photographic products to reduce or eliminate various problems associated with hydroquinones, including migration of hydroquinones within the product during storage and the discoloration of images on storage due to oxidation of hydroquinone present in an image-receiving element of the photographic product.

4 Claims, 7 Drawing Sheets

PROCESS AND COMPOSITION FOR USE IN PHOTOGRAPHIC MATERIALS CONTAINING HYDROQUINONES

BACKGROUND OF THE INVENTION

This invention relates to a process and composition for use in photographic materials containing hydroquinones. The process and composition of this invention are primarily intended for use in diffusion transfer films, which are usually referred to as "self-developing" or "instant" films.

The term "hydroquinone" is used herein generically to refer to any aromatic system in which a single phenyl ring bears two hydroxyl groups in positions oara to one another. Thus, the term as used herein includes not only derivatives of hydroquinone itself in which the phenyl ring is substituted, for example 2-phenyl-5-methylhydroquinone, but also compounds in which the phenyl ring bearing the hydroxyl groups is fused to one or more other aromatic rings, for example 1,4-dihydroxynaphthalene.

Hydroquinones have found widespread use as developers in photographic systems of both the conventional (wet-processed) and instant types; see, for example, Lee, W.E. and Brown, E.R., in Chapter 11 of James, T.H. (ed.), The theory of the photographic process, Macmillan, New York (1977). Many instant films (such as those described in, for example, Walworth, V.K. and Mervis, S.H., Instant photography and related reprographic processes, in Sturge, J., Walworth, V.K., and Shepp, A. (eds.), Imaging materials and processes—Neblette's eighth edition, Van Nostrand Reinhold, New York, NY (1989), and references cited therein, especially U.S. Pat. No. 2,983,606 to Rogers and U.S. Pat. No. 4,740,448 to Kliem) comprise a photosensitive element, an image-receiving element and a device (usually a disruptible pod) for contacting the photosensitive element with an alkaline developing composition. The photosensitive element has one or more silver halide emulsion layers each of which has associated therewith a dye developer, that is to say a compound which contains both a silver halide developing moiety and the chromophore of a dye. Upon exposure of the photosensitive element and contact of the alkaline developing composition therewith, in unexposed regions the dye developer diffuses to the image-receiving element. However, in exposed regions, the dye developer is oxidized and immobilized, so that no transfer of dye developer to the image-receiving element takes place. Thus, a positive image is formed on the image-receiving element.

While the dye developer may itself develop exposed silver halide, in practice the dye developer is used in conjunction with a colorless developing agent, sometimes referred to as an "auxiliary developer", "messenger developer" or "electron transfer agent". The auxiliary developer itself develops the exposed silver halide in exposed regions, and the oxidized auxiliary developer thus produced participates in a redox reaction with the dye developer, thereby oxidizing and immobilizing the dye developer. The auxiliary developer is usually a hydroquinone.

The photosensitive elements of instant films may also make use of processes in which a diffusible image dye is released from an immobile precursor by silver-initiated cleavage of certain sulfur-nitrogen containing compounds, such as thiazolidines. As described, for example, in the aforementioned U.S. Pat. No. 4,740,448, such thiazolidines are used in conjunction with a colorless developing agent or "primary developer", which is usually a hydroquinone.

Thus, the photosensitive elements of most instant films contain at least one hydroquinone, and color instant films may contain more than one hydroquinone. For example, the photosensitive elements described in Examples 2 and 3 of the aforementioned U.S. Pat. No. 4,740,448 each contain two separate layers each containing 4'-methylphenylhydroquinone (MPHQ) and a third layer containing 2-phenyl-5-t-butylhydroquinone.

Unfortunately, hydroquinones tend to be highly mobile in the polymeric media used in the photosensitive elements of instant films, especially at highly alkaline pH, and the mobility of the hydroquinones can cause various problems. Firstly, during development the hydroquinones tend to transfer to the image-receiving element with the dyes. Although the presence of hydroquinone in the image-receiving layer does not affect image formation upon extended storage the hydroquinone tends to be oxidized by atmospheric oxygen to the corresponding quinone, which may produce an undesirable yellow or straw color in white regions of the image. Secondly, in a color film containing a plurality of hydroquinone-containing layers, a hydroquinone intended for use with one dye may diffuse, either during storage before exposure or during development, into a layer containing a hydroquinone intended for use with a different dye. The presence of the "wrong" hydroquinone in a layer may cause color mixing, as discussed for example in U.S. Pat. No. 4,293,641 to Takahashi et al. These diffusion problems are exacerbated by the need to keep the individual layers of an instant film very thin (of the order of 1 $\mu$m) in order to provide a high resolution image within a reasonable development time.

The incorporation of hydroquinones into photosensitive elements of instant film units by conventional coating procedures also presents difficulties. Some hydroquinones cannot be dispersed in water, so that they must be coated from non-aqueous media, which present environmental and waste-disposal problems and costs. For example, in the aforementioned U.S. Pat. No. 4,740,448 t-butylhydroquinone is coated from a solution in diethyldodecanamide. Even where the hydroquinone can be coated from an aqueous dispersion, the hydroquinone is frequently susceptible to atmospheric oxidation during coating, and the presence of quinone in the photosensitive element not only effectively wastes part of the hydroquinone but may also lead to color distortion problems caused by the quinone oxidizing and immobilizing dye developer, even in unexposed areas of the photosensitive element.

It is known that hydroquinones will form hydrogen-bonded complexes with certain nitrogenous organic compounds, and attempts have been made to use such complexes in imaging systems. For example, U.S. Pat. No. 4,097,288 to Lawton, describes a heat sensitive recording composition containing normally colorless lactones or spiropyran compounds in combination with hydrogen bonded molecular complexes of phenolic compounds with amines or amides, these complexes having a dissociation temperature ranging from 50° to 220° C. The composition is stated to be less sensitive to pressure and less susceptible to background staining, image flooding, moisture sensitivity, odor, railroading and burnout problems as compared with compositions in which phenolic compounds are not complexed. Among the specific complexes disclosed are complexes of hydroquinone with acetamide and formamide.

The aforementioned U.S. Pat. No. 4,293,641 describes a photographic light-sensitive material comprising a support having at least two silver halide photographic emulsion layers capable of forming a silver image upon treatment with an alkaline processing solution in the presence of a developing agent for silver halide after exposure, and an interlayer positioned between the emulsion layers, this interlayer containing a complex formed from a mixture of hydroquinone derivatives having a solidifying point of 100° C. or less, and which are different compounds from the developing agent for silver halide used in the treatment of the material, and a homopolymer or copolymer containing pendant lactam rings. This interlayer is stated to substantially prevent color mixing. However, this proposed solution to the color mixing problem requires the provision of an additional layer in the photosensitive element, which layer must include a hydroquinone different from that used to develop the silver halide emulsion layers, and also requires the preparation of the polymer for the interlayer. This patent does not suggest any way of dealing with the problem of discoloration of the image caused by diffusion of hydroquinone to the image-receiving element.

It has now been found that complexes of hydroquinones with certain simple, monomeric diamides can be used in place of the hydroquinones themselves in instant films to reduce or overcome some of the problems associated with the use of hydroquinones in such films. In addition, the provision of these diamides at locations within the films where the diamides can form complexes with the diamides during or after development reduces or overcomes other problems associated with the use of hydroquinones in such films.

SUMMARY OF THE INVENTION

In one aspect, this invention provides a photographic product for forming a diffusion transfer image and comprising:

a photosensitive element comprising at least one photosensitive silver halide emulsion layer having associated therewith an image dye-providing material, the photosensitive element further comprising at least one hydroquinone, the photosensitive element being such that upon its exposure to light and contact with an alkaline developing composition, image dye is released from non-exposed regions of the photosensitive element; and an image-receiving element in superposed relationship or adapted to be placed in superposed relationship with the photosensitive element so as to receive image dye released from the photosensitive element and thereby form an image, at least one of the photosensitive element and the image-receiving element comprising a diamide of an aromatic dicarboxylic acid in which two carboxyl groups are arranged para to one another on the same phenyl ring, the diamide being an N,N,N',N'-tetrasubstituted diamide, in which each of the substituents on the amide nitrogen atoms is independently an alkyl, cycloalkyl or aryl group. These diamides will hereinafter be referred to as "tetrasubstituted para-diamides".

This invention also provides a photographic process which comprises:

imagewise exposing to actinic radiation a photographic product having a photosensitive element and an image-receiving element, the photosensitive element comprising at least one photosensitive silver halide emulsion layer having associated therewith an image dye-providing material, the photosensitive element further comprising at least one hydroquinone; and contacting the exposed photosensitive silver halide emulsion layers with an alkaline processing composition, and thereby effecting development of the exposed photosensitive silver halide emulsion layer, release of image dye from non-exposed areas of the emulsion layer and transfer of the released dye and some of the hydroquinone to the image-receiving element, thereby forming an image, wherein there is provided, in the image-receiving element or in a layer of the photographic product sensitive element lying between the image-receiving element and the exposed photosensitive silver halide emulsion layer, a tetrasubstituted para-diamide, this tetrasubstituted para-diamide serving to reduce the amount of hydroquinone transferred to the image-receiving element.

This invention also provides a process for forming a photographic product, which process comprises depositing upon a substrate at least one silver halide emulsion layer and at least one hydroquinone, the hydroquinone being deposited from an aqueous dispersion thereof, wherein the aqueous dispersion of the hydroquinone further comprises a tetrasubstituted para-diamide.

Finally, this invention provides a hydrogen-bonded complex of a hydroquinone with a tetrasubstituted para-diamide.

DETAILED DESCRIPTION OF THE INVENTION

As already mentioned, this invention provides a diffusion transfer photographic product in which at least one of the photosensitive element and the image-receiving element comprises a tetrasubstituted para-diamide. The para-diamide may serve several different purposes in such a photographic product, and the exact location or locations at which the para-diamide is incorporated depends upon the purpose which the para-diamide is intended to serve.

Firstly, the tetrasubstituted para-diamide may serve to provide an exposed image-receiving element substantially free from uncomplexed hydroquinone, either by preventing hydroquinone from reaching the image-receiving element during image formation, or by complexing any hydroquinone which does reach the image-receiving element. In either case, the para-diamide prevents oxidation of hydroquinone in the image-receiving element to the corresponding quinone, and thus avoids the yellowing problem sometimes experienced upon storage of conventional instant films. (The tetrasubstituted para-diamide complex of a hydroquinone is much less susceptible to oxidation than the free hydroquinone, so even if the complex is present in an image-receiving element during storage, oxidation of the hydroquinone and yellowing of the image are eliminated, or at least substantially reduced.) For this purpose, the para-diamide may be present in the image-receiving element or in a layer of the photosensitive element lying between the image-receiving element and the (or all of the) hydroquinone-containing layer(s) of the photosensitive element. In many cases, the image-receiving elements of commercial instant films comprise polymers having pendant pyridine rings and/or pendant substituted quaternary ammonium groups, and such nitrogen-containing polymers are highly compatible with tetrasubstituted para-diamides.

Secondly, the tetrasubstituted para-diamide may be present in at least one hydroquinone-containing layer of the photosensitive element, so that the paradiamide is complexed with the hydroquinone in this layer. In this position, the para-diamide serves to prevent diffusion of the hydroquinone from its proper layer during storage before exposure or during exposure. The presence of the para-diamide does not interfere with the developing action of the hydroquinone, since when the strongly alkaline developing composition reaches the hydroquinone-containing layer during development, the hydroquinone is deprotonated and the complex breaks down, leaving free hydroquinone to perform its developing action.

The tetrasubstituted para-diamide may, of course, also be present in one or more hydroquinone-containing layers of the photographic product as a result of being added to the hydroquinone prior to coating in order to assist in dispersing the hydroquinone in an aqueous medium. It should be noted that, when the para-diamide is used to assist dispersion of the hydroquinone in this manner, it is not necessary to add a quantity of para-diamide sufficient to complex all of the hydroquinone to be dispersed, since a much smaller quantity of para-diamide, typically from about 0.03 to about 0.5 mole of the para-diamide per mole of the hydroquinone, suffices to disperse the hydroquinone in an aqueous medium. For example, 0.05 mole of N,N,N',N'-tetraethylterephthalamide per mole of 2-phenyl-5-methyl--hydroquinone renders the hydroquinone readily dispersible in water, although the free hydroquinone cannot be dispersed in water.

Thirdly, when the photosensitive element comprises at least two hydroquinone-containing layers, the tetrasubstituted para-diamide may be present in a layer disposed between the two hydroquinone-containing layers, thus preventing the hydroquinone in one hydroquinone-containing layer diffusing to the other hydroquinone-containing layer.

The tetrasubstituted para-diamides used in the present invention have essentially no tendency to hydrogen bond to themselves, and thus there is essentially no risk of the tetrasubstituted para-diamide auto-complexing instead of complexing with the hydroquinone. It is preferred that the para-diamide be a diamide of terephthalic acid, desirably an N,N,N',N'-tetraalkyl diamide of terephthalic acid; terephthalic acid diamides (which are known compounds; see, for example, Beilstein, Handbuch der Organische Chemie, E IV 9, page 3321, Syst-Nr. 978/H 845, and E III, page 4253) can easily be prepared from inexpensive, readily-available terephthaloyl chloride and the appropriate amine. Terephthalic acid diamides are also of low molecular weight, which reduces the amount of para-diamide which must be incorporated into a photographic product to complex any given amount of hydroquinone. Two especially preferred para-diamides for use in the present invention are N,N,N',N'-tetraethyl- and N,N,N',N'-tetramethyl-terephthalamides.

The hydroquinones used in the present invention may be any of those conventionally used as developing agents in photographic media, and include all those described, for example in the aforementioned U.S. Pat. Nos. 2,983,606 and 4,740,448. Preferred hydroquinones include t-butylhydroquinone, 2-phenyl-5-t-butylhydroquinone, 2-(4'-methyl)-phenyl-5-t-butylhydroquinone, 4'-methylphenylhydroquinone, 2-phenyl-5-methylhydroquinone and 2-hexyl-5-t-butylhydroquinone. As previously noted, complexing of 2-phenyl-5-methylhydroquinone prior to incorporation into photographic products is especially advantageous in that such complexing permits this hydroquinone to be coated from an aqueous dispersion, whereas the free hydroquinone cannot be dispersed in aqueous media.

The hydroquinone/para-diamide complexes can readily be formed from their constituents by grinding the hydroquinone and the tetrasubstituted para-diamide together in the solid state; for preparation of the complexes on a laboratory scale, simple stirring of a mixture of the hydroquinone and para-diamide, or micromilling of such a mixture in a conventional laboratory mill gives good results.

Figure 1:
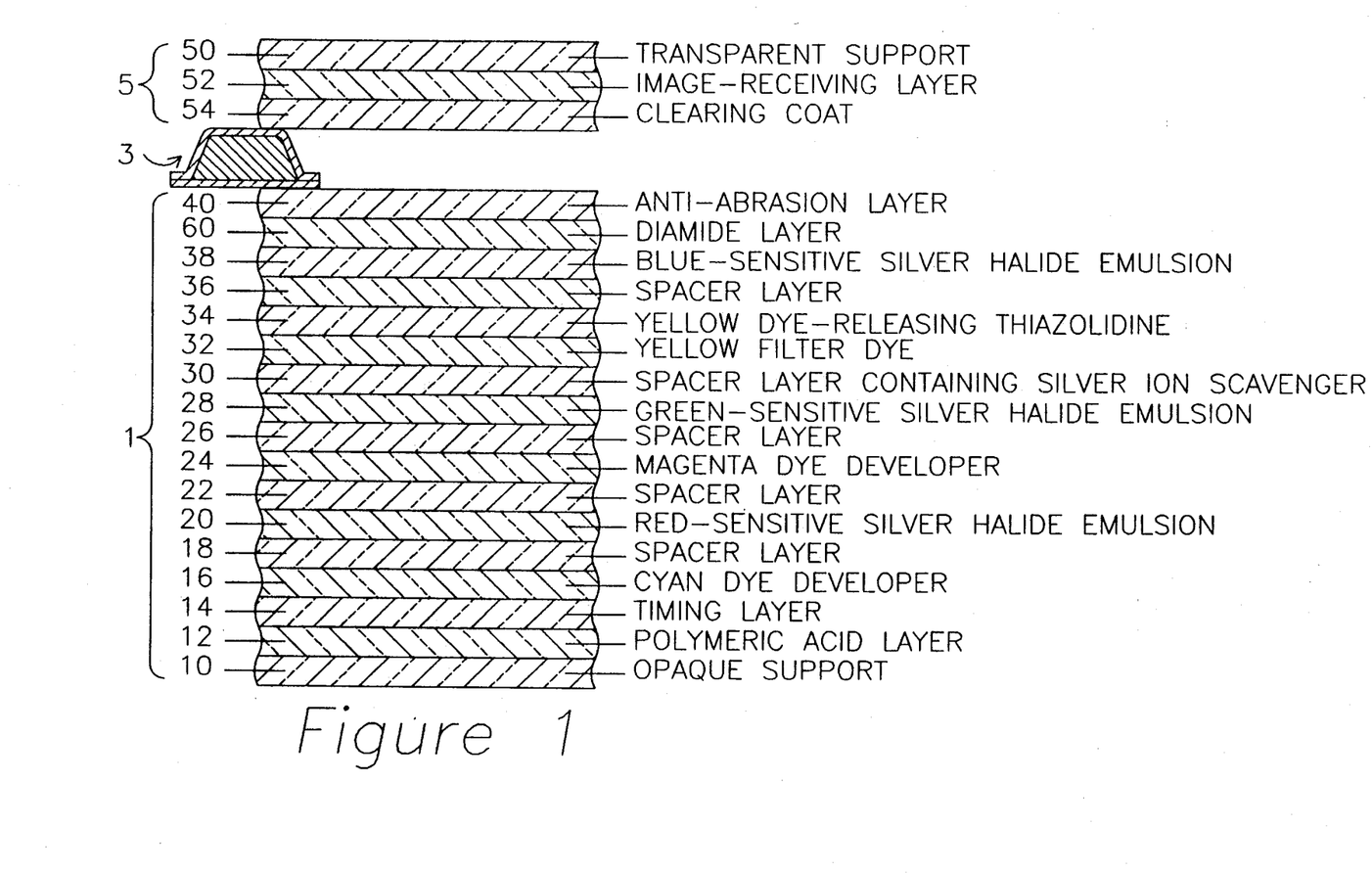
FIG. 1 is a schematic cross-section through an instant color film of the type described in the aforementioned U.S. Pat. No. 4,740,448, showing where a tetrasubstituted para-diamide or a complex of a tetrasubstituted para-diamide and a hydroquinone may be used in accordance with the present invention.

FIG. 1 of the accompanying drawings illustrates a diffusion transfer film unit of the type disclosed in the aforementioned U.S. Pat. No. 4,740,448, which is adapted to provide integral negative-positive reflection prints and employing cyan and magenta dye developers as the image dyes to form the cyan and magenta colors, and a yellow image dye-releasing thiazolidine.

FIG. 1 illustrates a diffusion transfer film unit comprising a photosensitive component or element 1 shown in superposed relationship with a transparent image-receiving ("positive") component or element 5 through which photoexposure of the photosensitive element is to be effected. A rupturable container or pod 3 releasably holding a processing composition is positioned between the photosensitive and image-receiving elements 1 and 5. The photosensitive element 1 comprises an opaque support 10 carrying, in sequence, a neutralizing layer 12 of a polymeric acid, a layer 14 adapted to time the availability of the polymeric acid by preventing diffusion of the processing composition thereto for a predetermined time, a cyan dye developer layer 16, a spacer layer 18, a red-sensitive silver halide emulsion layer 20, a spacer layer 22, a magenta dye developer layer 24, a spacer layer 26, a green-sensitive silver halide emulsion layer 28, a spacer layer 30 containing a silver ion scavenger, a yellow filter dye layer 32, a layer 34 of a yellow image dye-releasing thiazolidine, a spacer layer 36 containing a colorless silver halide developing agent, a blue-sensitive silver halide emulsion layer 38, and a top coat or anti-abrasion layer 40. The image-receiving element or component 5 comprises a transparent support 50 carrying, in sequence, an image-receiving layer 52 and a clearing coat 54. Photoexposure is effected through the transparent support 50 and the layers carried thereon, which are also transparent, the film unit being so positioned in the camera that light admitted through the camera exposure or lens system is incident upon the outer or exposure surface of the transparent support 40. After exposure the film unit is advanced between suitable pressure applying members or rollers (not shown), rupturing the pod 3 thereby releasing and distributing a layer of an opaque processing composition containing titanium dioxide and pH-sensitive optical filter agents or dyes as taught in U.S. Pat. No. 3,647,347, thereby forming a laminate of the photosensitive element, and the image-receiving element 5 with their respective supports providing the outer layers of the laminate. The processing composition contains a film-forming, viscosity-providing polymer and has an initial pH at which the optical filter agents contained therein are colored; the optical filter agents are selected to exhibit the appropriate light absorption, i.e., optical density, over the wavelength range of ambient light actinic to the photosensitive element. As a result, ambient or environmental light within that wavelength range incident upon the surface of transparent support 50 and transmitted traversely through the transparent support and the transparent layers carried thereon in the direction of the exposed silver halide emulsions is absorbed, thereby avoiding further exposure of the photoexposed and developing silver halide emulsions. Exposed blue-sensitive silver halide is developed by a colorless silver halide developing agent initially present in spacer layer 36. Unexposed blue-sensitive silver halide is dissolved by a silver solvent initially present in the processing composition and transferred to the layer 34 containing a yellow image dye-releasing thiazolidine. Reaction with the complexed silver initiates a cleavage of the thiazolidine ring and release of a diffusible yellow image dye, as described, for example, in Cieciuch, et al. U.S. Pat. Nos. 3,719,489 and 4,098,783.

Development of the exposed green-sensitive and red-sensitive silver halide, preferably by a messenger developer, e.g. 4'-methylphenylhydroquinone, results in the imagewise immobilization of the magenta and cyan dye developers, respectively. Unoxidized magenta and cyan dye developers in unexposed areas of the green- and red-sensitive silver halide emulsions remain diffusible and transfer to the image-receiving layer 52 through the developed blue-sensitive silver halide emulsion layer 38. Transfer of the imagewise released yellow image dye and the imagewise unoxidized magenta and cyan dye developers to the image-receiving layer is effective to provide the desired multicolor transfer image.

Permeation of the alkaline processing composition through the timing layer 14 to the neutralizing (polymeric acid) layer 12 is so controlled that the process pH is maintained at a high enough level to effect the requisite development and image transfer and to retain the optical filter agents in colored form within the processing composition layer and on the silver halide emulsion side of the layer, after which pH reduction effected as a result of alkali permeation into the polymeric acid layer 12 is effective to reduce the pH to a level which changes the optical filter agents to a colorless form. Absorption of the water from the applied layer of the processing composition results in a solidified film composed of the film-forming polymer and the white pigment dispersed therein, thus providing a light-reflecting layer which also serves to laminate together the photosensitive component 1 and the image-receiving component 5 to provide the final integral image. The positive transfer image present in the image-receiving layer 54 is viewed through the transparent support 50 against the light-reflecting layer which provides an essentially white background for the dye image and also effectively masks from view the developed photosensitive element 1.

The film unit shown in FIG. 1 will normally include three separate hydroquinone-containing layers, one associated with each of the three silver halide emulsion layers. The hydroquinone may be present in the silver halide emulsion layer itself, in the layer containing the dye developer or dye-releasing material or in a spacer layer between the layer containing the dye developer or dye-releasing material and the silver halide emulsion layer. Example 3 of the aforementioned U.S. Pat. No. 4,740,448, for instance, has MPHQ present in the cyan dye developer layer 16 and in the green-sensitive silver halide emulsion layer 28, and 2-phenyl-5-t-butylhydroquinone present in the spacer layer 38.

The para-diamide may be incorporated into various layers of the film unit shown in FIG. 1 depending upon which problem, or combination of problems, it is desired to overcome. If it is desired to avoid the presence of free hydroquinone in the image-receiving layer 52, the para-diamide may be included in the image-receiving layer 52 itself or in any layer lying between this layer and one or more of the hydroquinone-containing layers. Thus, for example, the para-diamide may be included in the image-receiving layer 52, the clearing coat 54, the anti-abrasion layer 40, or in an additional diamide layer 60 disposed between the anti-abrasion layer 40 and the spacer layer 38. However, as already noted, it is usually most convenient to include the para-diamide in the image-receiving layer 52, since the para-diamide is highly compatible with the nitrogenous polymers used in most commercial image-receiving layers.

If it is desired to stabilize the hydroquinone or if the para-diamide is used to assist coating of the hydroquinone, the para-diamide will be included in the hydroquinone-containing layer itself, and thus in FIG. 1 could be included in any one or more of the cyan dye developer layer 16, the green-sensitive silver halide emulsion layer 28, and the spacer layer 38.

Finally, if it is desired to use the para-diamide to prevent migration of one hydroquinone to a layer containing a different hydroquinone, the para-diamide may be placed in any layer disposed between the two hydroquinone-containing layers, for example in any one or more of the layers 18, 20, 22, 24, 26, 30, 32, 34 and 36 in FIG. 1, or in an additional diamide layer interposed between any two of these layers.

The use of para-diamides in photographic products in accordance with the present invention reduces or eliminates many of the problems normally associated with the preparation and use of hydroquinones in such photographic products, including difficulties in incorporating the hydroquinones into the product, migration of the hydroquinones within the product during storage, and discoloration of the image during storage caused by the presence of free and oxidizable hydroquinone in the image.

Although the invention has been illustrated above with reference to a diffusion transfer photographic film unit of one particular integral type (namely the type used in the aforementioned U.S. Pat. No. 4,740,448), the use of para-diamides in accordance with the present invention can also be practiced in other integral film units and in "peel-apart" film units such as those illustrated in U.S. Pat. Nos. 2,627,460; 2,983,606 and 3,362,819.

The following Examples are now given, though by way of illustration only, to show details of particularly preferred reagents, materials, conditions and techniques used in forming and carrying out the photographic products and processes of the present invention, and producing the hydroquinone/para-diamide complexes.

Example 1 : Preparation and structures of complexes of hydroquinone with N,N,N',N'-tetraethyl- and N,N,N',N'-tetramethylterephthalamide Part A : Formation and properties of complexes N,N,N',N'-tetraethyl- and N,N,N',N'-tetramethyl-terephthalamide were prepared by condensation of terephthaloyl chloride with diethylamine and dimethylamine respectively. The products were purified by recrystallization from ethanol and their purity confirmed by comparison with the melting points given in Beilstein, Handbuch der Organische Chemie, E IV 9, page 3321, Syst-Nr. 978/H 845, and E III, page 4253.

Mixtures of these two para-diamides and hydroquinone in molar ratios of 3:1, 2:1, 1:1, 1:2 and 1:3 were prepared by grinding the two materials together using either a Bel-Art Products MicroMill mill (sold by VWR Scientific, P.O. Box 13645, Philadelphia PA 19101-9711) for four hours, or by shaking less than 2 grams of mixture in a plastic container provided with a polytetrafluoroethylene coated stirring bar on a Vortex stirrer (sold by VWR Scientific) for four hours.

The mixtures thus prepared, together with the pure para-diamides and hydroquinone, were then tested by differential scanning calorimetry using a DuPont 9900 and a Perkin-Elmer DSC4 differential scanning calorimeter. Samples of from 1 to 3 mg. of each material were weighted into aluminum sample pans, then heated at 10° C per minute under a nitrogen atmosphere using a nitrogen purge rate of 30 mL/min.

All samples were also analyzed by $^{13}C$ cross-polarized magic angle spinning (CP/MAS) nuclear magnetic resonance (NMR) spectroscopy using a Bruker 200 MHz Fourier Transform NMR spectrometer.

The NMR spectra for the hydroquinone/ tetraethyl-diamide mixtures are given in Table 1 below; in this Table, $H_1$ denotes the resonance of the ring carbon atoms attached to the hydroxyl groups in the hydroquinone, $H_{2,3}$ denotes the resonance of the unsubstituted ring carbons in the hydroquinone, $T_{c=o}$ denotes the resonance of the carbonyl carbons of the diamide, $T_1$ denotes the resonance of the ring carbon atoms attached to the amide groups in the diamide, $T_{2,3}$ denotes the resonance of the unsubstituted ring carbons in the diamide, and $Et_1$ and $Et_2$ denotes respectively the resonances of the α- and β-carbon atoms of the ethyl groups in the diamide.

TABLE 1

| Molar Ratio | $T_{c=o}$ | $H_1$ | $T_1$ | $T_{2,3}$ | $H_{2,3}$ | $Et_1$ | $Et_2$ |
|---|---|---|---|---|---|---|---|
| H | — | 149.6 | — | — | 119.3 | — | — |
|   |   | 148.0 |   |   | 117.7 |   |   |
|   |   | 146.6 |   |   | 116.6 |   |   |
|   |   |   |   |   | 115.5 |   |   |
| H₃T | 170.9 | 148.9 | 137.6 | 127.1 | (118.6) | 41.2 | 14.1 |
|   | 167.8 | 147.2 |   | 125.3 | (117.1) | 39.4 | 13.3 |
|   |   |   |   | 122.6 | 114.7 | (37.6) | 12.5 |
|   |   |   |   |   | 113.8 | 34.5 | 11.1 |
| H₂T | 171.0 | 149.1 | 137.6 | 127.0 | 113.3 | 41.0 | 13.1 |
|   |   | 147.2 |   | 125.1 |   | 37.5 | 11.0 |
| HT | 171.0 | 149.2 | 137.6 | 127.0 | 113.3 | 41.1 | 13.2 |
|   |   |   |   | 125.1 |   | 37.5 | 11.0 |
|   |   |   |   |   |   | (34.5) |   |
| HT₂ | 171.0 | 149.3 | 137.6 | 127.1 | 113.5 | 41.2 | 14.1 |
|   | 167.8 |   |   | 125.3 |   | 39.5 | 13.3 |
|   |   |   |   | 122.7 |   | 36.2 | 12.4 |
|   |   |   |   |   |   | (35) | 11.1 |
|   |   |   |   |   |   | 34.5 |   |
| HT₃ | 169.7 | 149.3 | 137.6 | 125.3 | 113.5 | 41.2 | 14.1 |
|   | 167.8 |   |   | 122.6 |   | 39.5 | 12.5 |
|   |   |   |   |   |   | 36.2 |   |
|   |   |   |   |   |   | 34.5 |   |
| T | 169.7 | — | 137.6 | 125.3 | — | 41.1 | 14.1 |
|   | 167.8 |   |   | 122.6 |   | 39.5 | 12.3 |
|   |   |   |   |   |   | 36.2 |   |
|   |   |   |   |   |   | 34.5 |   |

Figure 2:
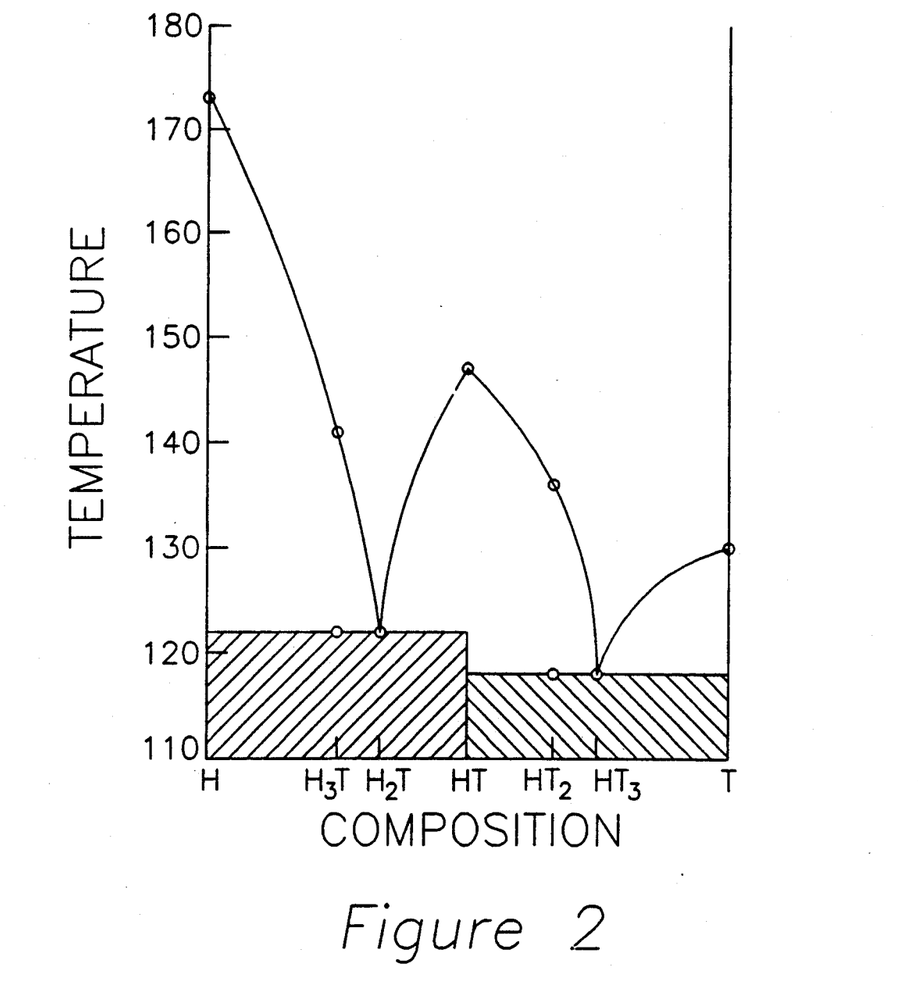
FIG. 2 is a phase diagram of the hydroquinone/N,N,N',N'-tetraethylterephthalamide system.

The results of the DSC analysis are summarized in the phase diagram of FIG. 2. Both the NMR and DSC analyses show the presence of a single 1:1 (molar ratio) complex of the hydroquinone and the diamide, with intermediate compositions between the 1:1 complex and the pure constituents showing the results expected for simple mixtures of the 1:1 complex with excess hydroquinone or diamide.

Specifically, in the pure hydroquinone, the ring carbons bearing the hydroxyl groups display a triplet resonance ($H_1$) at 148.1 ppm, whereas in the 1:1 mixture this resonance is simplified to a singlet at 149.2 ppm. In the HT₂ and HT₃ mixtures where there is no excess hydroquinone but there is excess diamide, no triplet at 148.1 ppm is observed. Furthermore, the chemical shifts of the unsubstituted ring carbons of the diamide serve as diagnostic resonances for those mixtures which contain free diamide. In the pure diamide, these carbons display a doublet at 124.0 ppm. The 1:1 mixture displays a doublet at 126.0 ppm, while intermediate mixtures show both the 124.0 and 126.0 ppm doublets in proportion to the excess diamide expected for the formation of a 1:1 complex. In the H₃T and H₂T mixtures which contain no free diamide, only the 126.0 ppm doublet is observed. Each of the other carbon resonances displays analogous behavior.

As will readily be apparent to any chemist, the phase diagram in FIG. 2 displays the classic form expected for two components which form a 1:1 complex; cf. the discussion of the analogous phenol/aniline system in Moore, W.J., Physical Chemistry, Prentice-Hall, New Jersey (1972), Chapter 7.

The NMR spectra for the hydroquinone/ tetramethyldiamide mixtures are given in Table 2 below; the designations for the various resonances are the same as those in Table 1 above, except that Me denotes the resonance of the methyl carbons of the diamide.

TABLE 2

| Molar Ratio | $T_{c=o}$ | $H_1$ | $T_1$ | $T_{2,3}$ | $H_{2,3}$ | Me |
|---|---|---|---|---|---|---|
| H | — | 149.5 | — | — | 119.4 | — |

TABLE 2-continued

| Molar Ratio | $T_{c=0}$ | $H_1$ | $T_1$ | $T_{2,3}$ | $H_{2,3}$ | Me |
|---|---|---|---|---|---|---|
| | | 148.1 | | | 118.0 | |
| | | 146.6 | | | 116.6 | |
| | | | | | 115.6 | |
| $H_3T$ | (171) | 149.5 | 137.2 | 126 | 119.4 | 38.5 |
| | 169.4 | 148.1 | | 124 | 117.9 | 34.8 |
| | | 146.6 | | | 115.6 | |
| $H_2T$ | (171) | 148.9 | 137.1 | 126.0 | 116.2 | 38.5 |
| | 169.4 | 148 | | 124.8 | 115.2 | 34.6 |
| HT | (171) | 151.0 | 138.0 | 129.0 | 116.0 | 37.6 |
| | 169.7 | | 135.8 | 124.9 | | 33.7 |
| $HT_2$ | (172) | 151.0 | 138.2 | 129.0 | 116.0 | 37.7 |
| | 169.8 | | 135.9 | 126.7 | | 33.7 |
| | | | | 125.0 | | |
| $HT_3$ | (172) | 150.9 | 138.3 | 129.0 | 116.0 | 38.7 |
| | 169.9 | | 135.8 | 126.7 | | 33.5 |
| | | | | 125.0 | | |
| T | (171.9) | — | 138.4 | 126.7 | — | (40.5) |
| | 170.0 | | | | | 38.7 |
| | | | | | | (35.2) |
| | | | | | | 33.4 |

Figure 3:
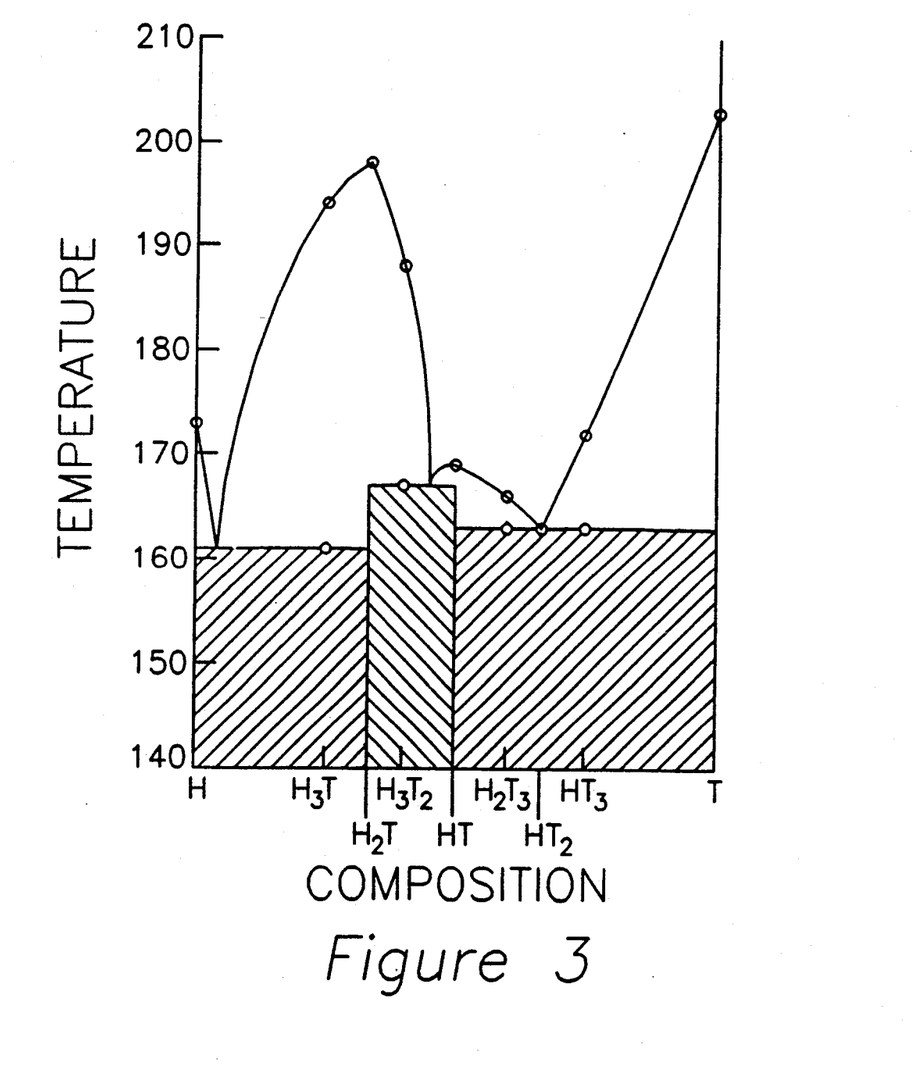
FIG. 3 is a phase diagram of the hydroquinone/N,N,N',N'-tetramethylterephthalamide system.

The results of the DSC analysis are summarized in the phase diagram of FIG. 3. For reasons explained below, this phase diagram includes additional mixtures having compositions $H_3T_2$ and $H_2T_3$. The $H_2T$ mixture exhibited a sharp endothermic transition at 198° C., and the HT mixture exhibited a sharp endothermic transition at 169° C.

The interpretation of these DSC and NMR results is more complicated than those for the tetraethyldiamide system discussed above, but are entirely consistent with the diamide forming both 1:1 and 1:2 complexes with the hydroquinone; it will be seen that the phase diagram is of the type expected for the formation of these two complexes. (The region of the phase diagram between the $H_2T$ and $HT_2$ mixtures was very difficult to interpret with only the original points, so the two additional intermediate mixtures shown in FIG. 3 were subjected to DSC analysis to provide the additional data points shown.)

Specifically, in the pure hydroquinone, the ring carbons bearing the hydroxyl groups display a triplet resonance ($H_1$) at 148.1 ppm, whereas in the $H_2T$ mixture this resonance is a very tight triplet at 148.5 ppm, while in the HT mixture the resonance is a singlet at 151.0 ppm. The observed resonance for $H_3T$ is consistent with this being a mixture of $H_2T$ and pure hydroquinone, while the resonances of both the $HT_2$ and $HT_3$ mixtures are consistent with them being mixtures of HT and pure diamide. A similar pattern is observed in the resonances for the unsubstituted ring carbons of the diamide; the singlet at 126.7 ppm in the pure diamide becomes an asymmetric pair of peaks at 129.0 and 124.9 ppm in the HT mixture and a tight doublet at 125.4 ppm in the $H_2T$ mixture. 25 Part B : X-ray crystal structures In view of the results achieved in Part A above, the 1:1 complex of hydroquinone with the tetraethyldiamide and the 2:1 complex of hydroquinone with the tetramethyldiamide were crystallized from ethanol and their structures determined by X-ray crystallography. The structures were found to be as follows:

1:1 complex of hydroquinone with the tetraethyldiamide
Triclinic, space group P1. a = 7.429 Å.
b = 7.723 Å. c = 10.035 Å. α = 71.23°. β = 89.64°.
γ = 81.58°
Atomic positions:

| Atom | x | y | z |
|---|---|---|---|
| C1 | 0.05276 | 0.55528 | 0.11019 |
| C2 | 0.05761 | 0.37070 | 0.12895 |
| H2 | 0.09273 | 0.27024 | 0.22343 |
| C3 | 0.00466 | 0.31489 | 0.01852 |
| H3 | 0.00706 | 0.16949 | 0.03946 |
| O4 | 0.09913 | 0.61987 | 0.21640 |
| H4 | 0.15460 | 0.51260 | 0.30100 |
| C5 | 0.11901 | 0.10625 | 0.53092 |
| C6 | −0.06604 | 0.16450 | 0.52238 |
| H6 | −0.11684 | 0.28537 | 0.54402 |
| C7 | 0.18503 | −0.05791 | 0.50742 |
| H7 | 0.32757 | −0.09464 | 0.50057 |
| C8 | 0.24789 | 0.22808 | 0.55375 |
| O9 | 0.26118 | 0.37426 | 0.45912 |
| N10 | 0.34694 | 0.17393 | 0.67451 |
| C11 | 0.30846 | 0.02507 | 0.79977 |
| H11A | 0.18009 | −0.00660 | 0.78233 |
| H11B | 0.28079 | 0.08810 | 0.88503 |
| C12 | 0.45948 | −0.13455 | 0.84522 |
| H12A | 0.41585 | −0.23939 | 0.93513 |
| H12B | 0.58915 | −0.10199 | 0.85983 |
| H12C | 0.49865 | −0.18099 | 0.75133 |
| C13 | 0.47993 | 0.28926 | 0.69338 |
| H13A | 0.53296 | 0.34698 | 0.59454 |
| H13B | 0.58016 | 0.20028 | 0.75814 |
| C14 | 0.39889 | 0.43373 | 0.75608 |
| H14A | 0.28676 | 0.51504 | 0.69742 |
| H14B | 0.49256 | 0.48614 | 0.77662 |
| H14C | 0.33726 | 0.39334 | 0.84122 |
| C1A | −0.05276 | 0.44472 | −0.11019 |
| C2A | −0.05761 | 0.62930 | −0.12895 |
| H2A | −0.09272 | 0.72976 | −0.22343 |
| C3A | −0.00466 | 0.68511 | −0.01852 |
| H3A | −0.00705 | 0.83051 | −0.03946 |
| O4A | −0.09913 | 0.38013 | −0.21640 |
| H4A | −0.15460 | 0.48741 | −0.30100 |
| C5A | −0.11901 | −0.10624 | 0.46908 |
| C6A | 0.06604 | −0.16450 | 0.47762 |
| H6A | 0.11684 | −0.28537 | 0.45598 |
| C7A | −0.18503 | 0.05791 | 0.49258 |
| H7A | −0.32757 | 0.09464 | 0.49943 |
| C8A | −0.24789 | −0.22808 | 0.44625 |
| O9A | −0.26118 | −0.37426 | 0.54088 |
| N10A | −0.34694 | −0.17393 | 0.32550 |
| C11A | −0.30846 | −0.02507 | 0.20024 |
| H11C | −0.18009 | 0.00660 | 0.21767 |
| H11D | −0.28079 | −0.08809 | 0.11497 |
| C12A | −0.45948 | 0.13455 | 0.15478 |
| H12D | −0.41585 | 0.23939 | 0.06488 |
| H12E | −0.58915 | 0.10199 | 0.14017 |
| H12F | −0.49865 | 0.18099 | 0.24868 |
| C13A | −0.47993 | −0.28926 | 0.30662 |
| H13C | −0.53296 | −0.34697 | 0.40546 |
| H13D | −0.58016 | −0.20028 | 0.24186 |
| C14A | −0.39889 | −0.43373 | 0.24392 |
| H14D | −0.28676 | −0.51503 | 0.30258 |
| H14E | −0.49256 | −0.48613 | 0.22338 |
| H14F | −0.33726 | −0.39334 | 0.15879 |

Figure 4:
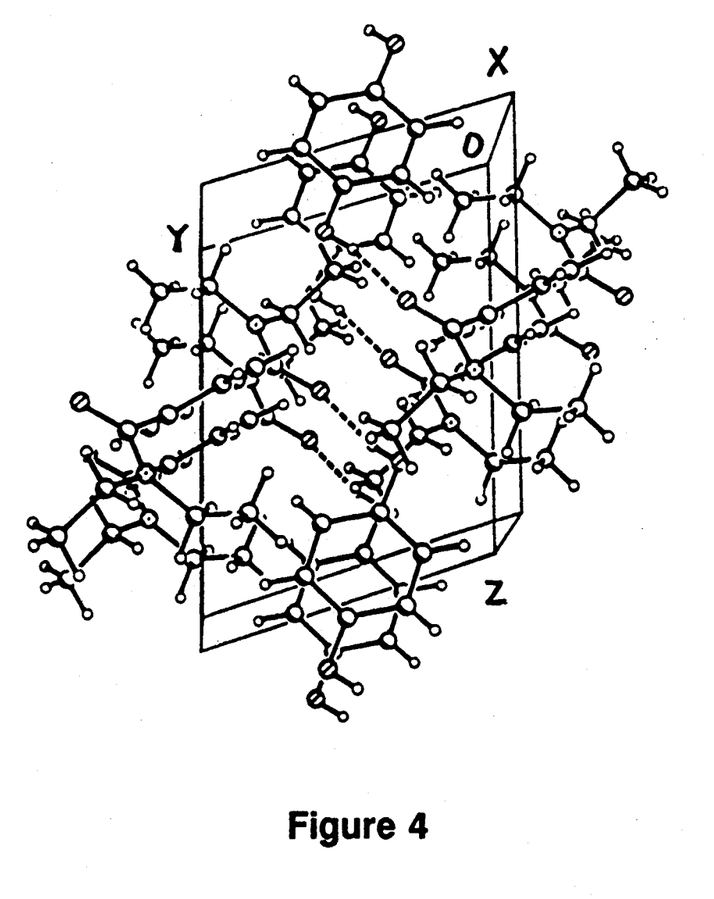
FIG. 4 shows the unit cell, as determined by X-ray crystallography, of the 1:1 complex formed by hydroquinone and N,N,N',N'-tetraethylterephthalamide.
Figure 5:
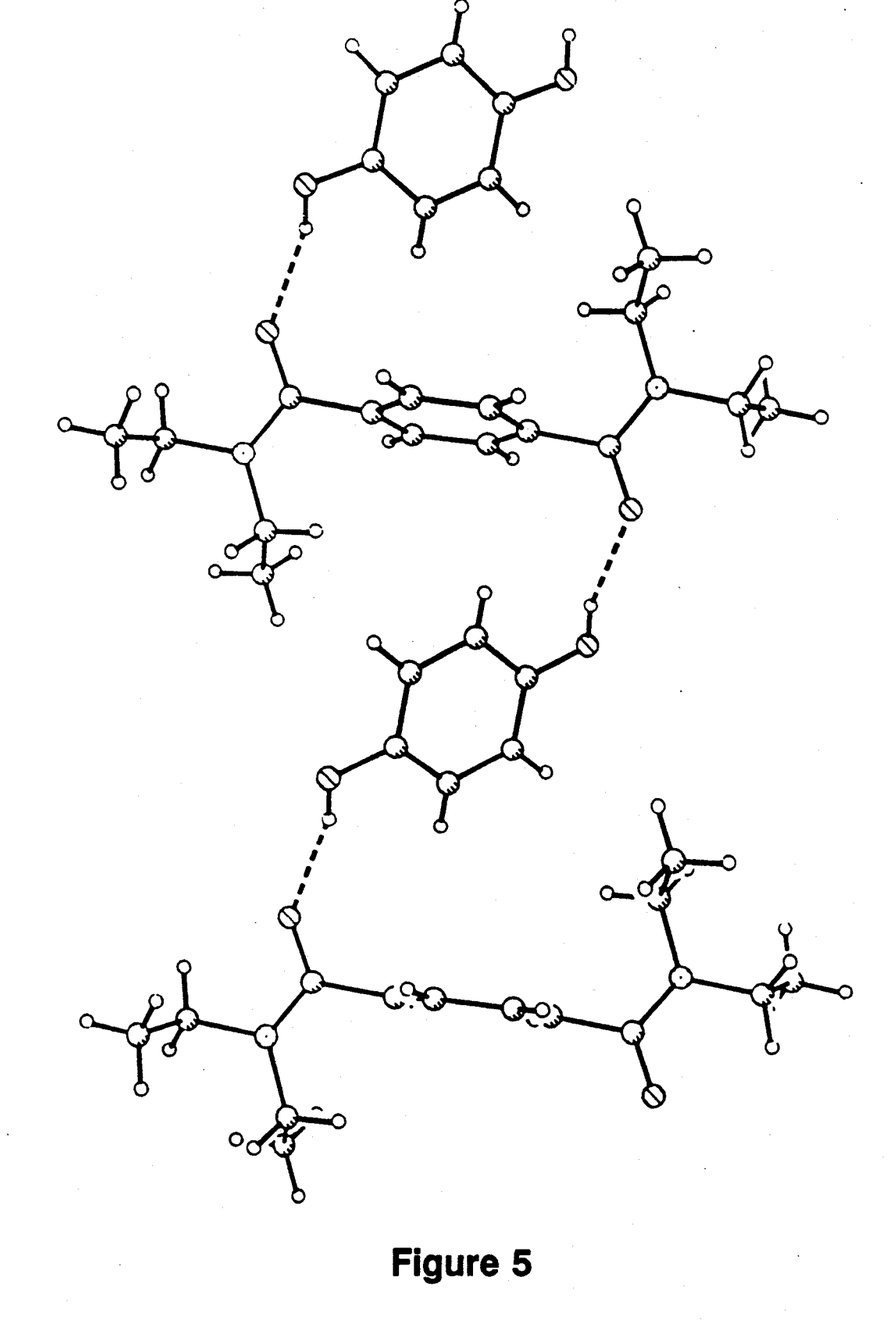
FIG. 5 shows an enlarged view of part of the unit cell shown in FIG. 3 showing in more detail the hydrogen bonds in the structure.

FIG. 4 of the accompanying drawings show the unit cell of the crystal, while FIG. 5 is an enlarged view of part of the unit cell showing more precisely the hydrogen bond between a hydroquinone oxygen and a para-diamide oxygen. The bond distances and angle for this hydrogen bond are:

H(4)—O(9) = 198 Å 
O(4)—O(9) = 2.73 Å
O(4)—H(4)—O(9) = 160.7°.

From FIGS. 4 and 5, it will be seen that in both cases hydrogen bonds between the hydroquinone hydroxyl groups and the carbonyl oxygens of the diamide link the hydroquinone and diamide together in infinite, alternating chains, with π-stacking taking place between a diamide phenyl ring in one chain and a hydroquinone phenyl ring in an adjacent chain.

2:1 complex of hydroquinone with the tetramethyldiamide
Triclinic, space group P1̄, a = 6.891 A.
b = 8.009 A, c = 10.916 A, α = 74.72°, β = 86.74°,
γ = 88.34°
Atomic positions:

| Atom | x | y | z |
|---|---|---|---|
| C1 | 0.45099 | 0.12432 | −0.10899 |
| C2 | 0.59592 | 0.00132 | −0.11791 |
| C3 | 0.35527 | 0.12364 | 0.00689 |
| C4 | 0.40987 | 0.26588 | −0.22711 |
| O5 | 0.52884 | 0.38194 | −0.26773 |
| N6 | 0.24672 | 0.26081 | −0.28523 |
| C7 | 0.09978 | 0.12317 | −0.24301 |
| C8 | 0.20829 | 0.40425 | −0.40118 |
| C9 | 0.33537 | 0.07090 | 0.43708 |
| C10 | 0.50477 | 0.16694 | 0.41723 |
| C11 | 0.67259 | 0.09617 | 0.48098 |
| O12 | 0.16795 | 0.13426 | 0.37616 |
| C13 | 0.08668 | −0.51222 | 0.11339 |
| C14 | 0.91816 | −0.60586 | 0.11388 |
| C15 | 0.16903 | −0.40627 | 0.00153 |
| O16 | 0.16887 | −0.53085 | 0.22889 |
| C1A | 0.54901 | −0.12432 | 0.10900 |
| C2A | 0.40408 | −0.00132 | 0.11791 |
| C3A | 0.64473 | −0.12364 | −0.00689 |
| C4A | 0.59014 | −0.26588 | 0.22711 |
| O5A | 0.47116 | −0.38194 | 0.26773 |
| N6A | 0.75328 | −0.26081 | 0.28523 |
| C7A | 0.90023 | −0.12317 | 0.24301 |
| C8A | 0.79171 | −0.40425 | 0.40118 |
| C9A | 0.66463 | −0.07090 | 0.56292 |
| C10A | 0.49523 | −0.16694 | 0.58277 |
| C11A | 0.32740 | −0.09617 | 0.51902 |
| O12A | 0.83204 | −0.13426 | 0.62384 |
| C13A | 0.91332 | −0.48777 | −0.11339 |
| C14A | 0.08184 | −0.39414 | −0.11388 |
| C15A | 0.83097 | −0.59373 | −0.00153 |
| O16A | 0.83113 | −0.46914 | −0.22889 |

Figure 6:
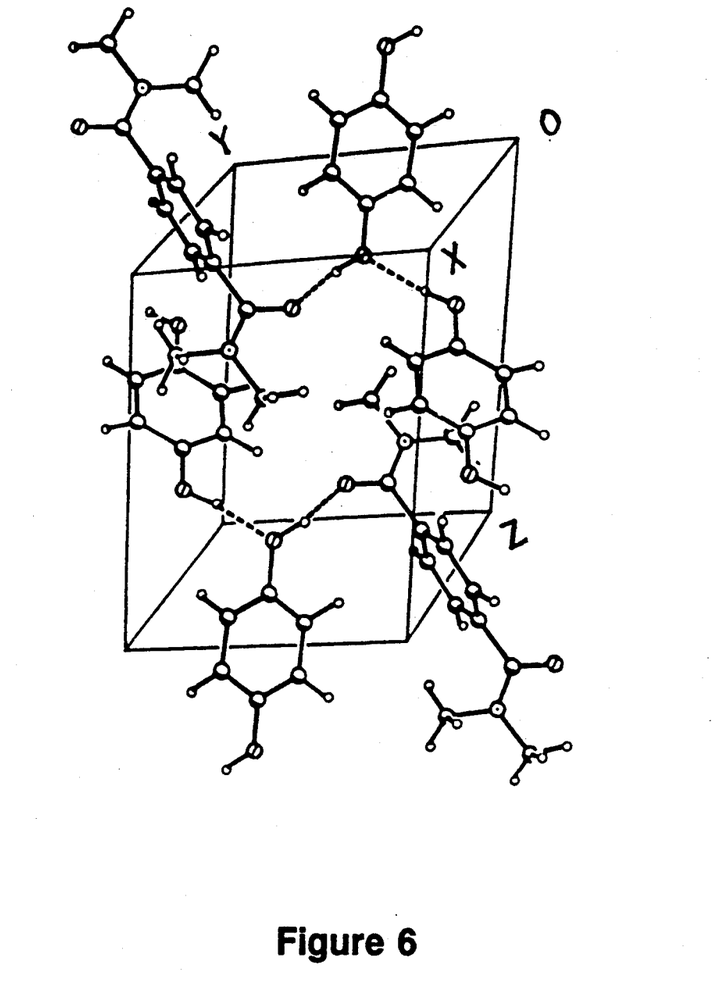
FIG. 6 shows the unit cell, as determined by X-ray crystallography, of the 2:1 complex formed by hydroquinone and N,N,N',N'-tetramethylterephthalamide.
Figure 7:
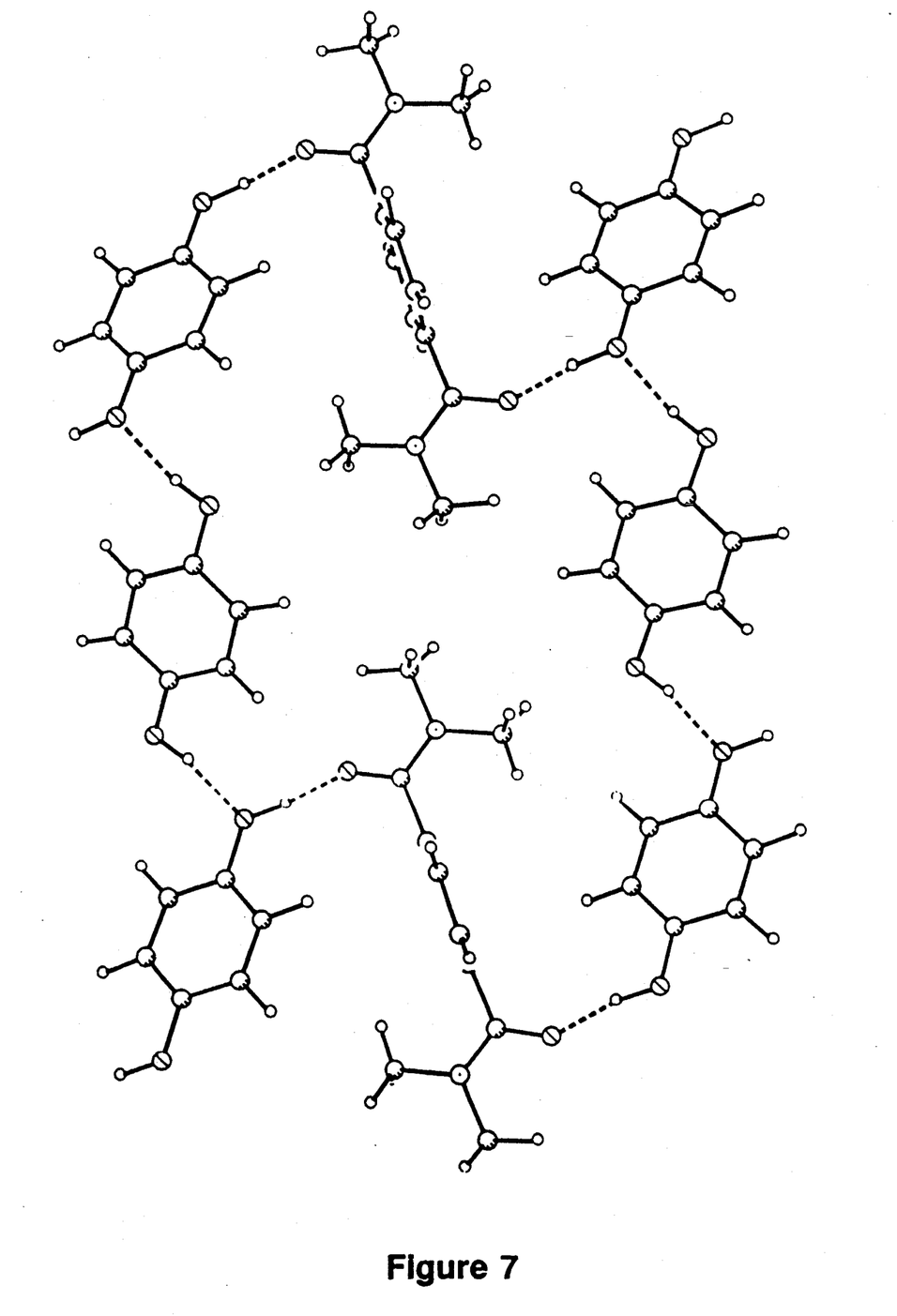
FIG. 7 shows an enlarged view of part of the unit cell shown in FIG. 6 showing in more detail the hydrogen bonds in the structure.

FIG. 6 of the accompanying drawings shows the unit cell of the crystal, while FIG. 7 is an enlarged view of part of the unit cell showing more precisely the hydrogen bonds between a hydroquinone oxygen and a para-diamide oxygen, and between this hydroquinone oxygen and an oxygen on a second molecule of hydroquinone. The bond distances and angles for these hydrogen bonds are:

H(12)—O(16) = 1.85 Å
O(12)—O(16) = 2.74 Å
O(12)—H(12)—O(16) = 165.6°
H(16)—O(5) = 1.56 Å
O(16)—O(5) = 2.60 Å
O(16)—H(16)—O(5) = 165.2°.

From FIGS. 6 and 7, it will be again be seen that the hydrogen bonds between the hydroquinone hydroxyl groups and the carbonyl oxygens of the diamide link the hydroquinone and diamide together in infinite, alternating chains, with π-stacking taking place between a diamide phenyl ring in one chain and a hydroquinone phenyl ring in an adjacent chain. The ability of the tetramethyldiamide to form the 1:2 complex with hydroquinone appears to be a packing phenomenon; while a second molecule of hydroquinone can be fitted into the lattice when methyl substituents are present, it appears that no "extra" hydroquinones can be accommodated when ethyl substituents are present.

Example 2 : Preparation of aqueous dispersions

This part illustrates the stabilization of an aqueous dispersion of easily-oxidizable hydroquinones by the formation of a complex of the present invention.

A 1:1 complex of N,N,N',N'-tetraethyl-phthalamide (BETP) and 2-phenyl-5-methylhydroquinone was prepared by grinding the constituents together in the same way as in Example 1. An aqueous dispersion of this complex was prepared by mixing with an ultrasonifier one part by weight of the complex, 2.92 parts by weight of water, 0.05 parts by weight of Tamol 731 surfactant and 0.03 parts by weight of ascorbyl palmitate. The resultant dispersion was stable and was not air-oxidized at ambient temperature; in contrast, a similar dispersion of the free hydroquinone was air-oxidized at ambient temperature.

A 1:1 complex of N,N,N',N'-tetraethyl-phthalamide and 2-phenyl-5-t-butylhydroquinone (PtBHQ) was prepared by grinding the constituents together in the same way. Aqueous dispersions were prepared by mixing with an ultrasonifier varying amounts of this complex, sufficient uncomplexed PtBHQ to provide, per 100 parts by weight of the aqueous dispersion, a total of 20 parts by weight of PtBHQ, 1 part by weight of Tamol 731 surfactant, 0.6 parts by weight of ascorbyl palmitate, 3 parts by weight of 2-phenyl-5-t-butylbenzoquinone (PtBBHQ), 3 parts by weight of gelatin and 0.2 parts by weight of sodium cellulose sulfate. These dispersions were placed in an oven at 42.5° C. and held at this temperature for 1028 hours, during which time samples were analyzed for PtBHQ, PtBBQ and BETP by gas-liquid chromatography. To provide a numerical measure of the rate of PtBHQ oxidation, the PtBHQ concentration, relative to its initial value, was plotted against time and the slope of the straight-line fit of the resultant data from 0 to 91 hours storage was calculated.

The table below shows the initial concentrations of PtBHQ, PtBBQ and BETP in the dispersions, the initial PtBHQ/BETP ratio, the aforementioned slope and the proportion of PtBHQ oxidized after 1028 hours storage.

TABLE 3

| Dispersion | Initial PtBHQ conc., wt % | Initial PtBBQ conc., wt % | Initial BETP conc., wt % | PtBHQ BETP ratio | Slope (× 10⁻³) | % PtBHQ oxidized |
|---|---|---|---|---|---|---|
| A | 2.94 | 0.63 | 0 | 0 | −3.84 | 34 |
| B | 3.30 | 0.64 | 0.22 | 15 | −2.84 | 33 |
| C | 3.25 | 0.65 | 0.41 | 7.9 | −3.39 | 31 |
| D | 2.99 | 0.58 | 0.72 | 4.2 | −3.51 | 27 |
| E | 3.01 | 0.63 | 1.81 | 1.7 | −1.91 | 19 |

From the foregoing, it will be seen that the addition of the para-diamide BETP to the hydroquinone substantially reduced the oxidation of the hydroquinone under the storage conditions used, addition of 1 mole of BETP per 1.7 moles of hydroquinone reducing the oxidation of the hydroquinone by about 50%.

Example 3 : Preparation of photographic product

This Example illustrates the improved stability of a photographic product which can be achieved by replacing the free hydroquinone used in such a product with a para-diamide complex of the same hydroquinone in accordance with the present invention.

Control film units (Film A) were prepared in and the aforementioned U.S. Pat. No. 4,740,448. These film units contained 2-phenyl-5-t-butylhydroquinone in the spacer layer 38. Film units of the present invention were prepared similarly except that the free 2-phenyl-5-t-butylhydroquinone was replaced by a complex of this hydroquinone with bis-N,N-dibutylterephthalamide (Film B) or bis-N,N-diethylterephthalamide (Film C). Samples of each type of film unit were stored at ambient temperature for six days, while other samples of each type of film unit were stored at 120° F. (49° C.) for the same period. The film units were then used to image a standard target and the maximum optical densities ($D_{max}$) and speeds (in log E units, at 0.75 optical density) of all the films in both blue and green were then determined using an automatic reading densitometer. (Although the para-diamide complex was only used in the spacer layer adjacent the blue-sensitive emulsion, the presence of this complex affects the green speed of the film because of the tendency for the 2-phenyl-5-t-butylhydroquinone to migrate through the film upon storage. The results of both the maximum optical density and speed tests are reported in Table 4 below as the values for the films stored at high temperature and the difference ($\Delta$) between the films stored at high temperature and the films stored at ambient temperature

TABLE 4

| Film | $D_{max}$ | | | | Speed | | | |
| --- | --- | --- | --- | --- | --- | --- | --- | --- |
| | Absolute | | $\Delta$ | | Absolute | | $\Delta$ | |
| | Green | Blue | Green | Blue | Green | Blue | Green | Blue |
| A | 2.05 | 1.93 | +0.07 | +0.33 | 1.50 | 1.64 | −0.22 | −0.32 |
| B | 1.85 | 1.41 | −0.10 | +0.05 | 1.63 | 1.76 | −0.11 | −0.18 |
| C | 1.90 | 1.42 | −0.04 | +0.19 | 1.62 | 1.71 | −0.12 | −0.22 |

From the data in Table 4, it will be seen that the incorporation of the 2-phenyl-5-t-butylhydroquinone in the form of either para-diamide complex substantially improved the stability of hydroquinone upon high temperature storage. In particular, the change in blue maximum density after storage was approximately halved, and the changes in both blue and green speeds were also approximately halved.

I claim:

1. A hydrogen-bonded complex of a hydroquinone with a diamide of an aromatic dicarboxylic acid in which two carboxyl groups are arranged para to one another on the same phenyl ring, the diamide being an N,N,N',N'-tetrasubstituted diamide, in which each of the substituents on the amide nitrogen atoms is independently an alkyl, cycloalkyl or aryl group.

2. A complex according to claim 1 wherein the diamide is a diamide of terephthalic acid 3. A complex according to claim 2 wherein the diamide is an N,N,N',N'-tetraalkylterephthalamide.

4. A complex according to claim 3 wherein the diamide is N,N,N',N'-tetraethyl or N,N,N',N'-tetramethylterephthalamide.

* * * * *